United States Patent
Prakash et al.

(10) Patent No.: US 8,801,709 B2
(45) Date of Patent: Aug. 12, 2014

(54) ENDOSCOPIC INSTRUMENT FOR TISSUE IDENTIFICATION

(75) Inventors: Mani N. Prakash, Boulder, CO (US); Timothy J. Bahney, Portland, OR (US); Darren Odom, Longmont, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/539,875

(22) Filed: Jul. 2, 2012

(65) Prior Publication Data

US 2012/0271307 A1 Oct. 25, 2012

Related U.S. Application Data

(62) Division of application No. 12/366,298, filed on Feb. 5, 2009, now Pat. No. 8,221,418.

(60) Provisional application No. 61/026,788, filed on Feb. 7, 2008.

(51) Int. Cl.
*A61B 18/18* (2006.01)

(52) U.S. Cl.
USPC ........................................................ 606/51

(58) Field of Classification Search
CPC .................. A61F 9/00745; A61B 2217/005; A61B 17/22012; A61B 2017/320084; A61B 2018/00011; A61B 18/1492; A61B 2018/00577; A61B 2218/002; A61B 2018/00214; A61B 18/1477; A61B 18/1402; A61B 18/1206; A61B 18/14; A61B 2018/00702; A61B 2018/00476; A61B 2018/00452; A61B 17/30; A61B 2018/00178; A61B 2018/00601; A61B 2018/126; A61B 18/149; A61B 18/1485; A61B 2018/1861; A61B 18/1482; A61B 2018/00196; A61B 2018/1407; A61B 17/32056; A61B 2018/141; A61B 18/1445; A61B 18/042; A61B 2218/007; A61B 18/1442; A61B 2013/0063; A61B 2018/00404; H01H 2300/014; A45D 26/0042; A61N 1/0424

USPC ........ 604/22; 606/41, 48, 50, 51, 34; 600/372

See application file for complete search history.

(56) References Cited

U.S. PATENT DOCUMENTS

| D223,367 S | 4/1972 | Kountz |
| D263,020 S | 2/1982 | Rau, III |

(Continued)

FOREIGN PATENT DOCUMENTS

| CN | 1103807 | 6/1995 |
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Manuel Mendez

(57) ABSTRACT

The present disclosure relates to various apparatus, systems and methods of identifying and treating tissue using at least one electrical property of tissue. Provided is a method for identifying and treating tissue, the method including providing a electrosurgical treatment device including an electrode assembly for measuring one or more electrical properties of a target tissue, the electrode assembly being mounted on a distal end thereof, measuring the one or more electrical characteristics of the target tissue, comparing the measured electrical property values of the target tissue against electrical property values of known tissue types, identifying a tissue type of the target tissue, adjusting an energy delivery configuration of the electrosurgical treatment device to the type of target tissue, and activating the electrosurgical treatment device to treat the target tissue.

15 Claims, 9 Drawing Sheets

(56) References Cited

U.S. PATENT DOCUMENTS

| | | | |
|---|---|---|---|
| D266,842 S | 11/1982 | Villers et al. | |
| D278,306 S | 4/1985 | McIntosh | |
| 4,543,959 A | 10/1985 | Sepponen | |
| D295,893 S | 5/1988 | Sharkany et al. | |
| D295,894 S | 5/1988 | Sharkany et al. | |
| D354,218 S | 1/1995 | Van de Peer | |
| 5,460,182 A | 10/1995 | Goodman et al. | |
| 5,500,012 A | 3/1996 | Brucker et al. | |
| 5,702,390 A * | 12/1997 | Austin et al. | 606/48 |
| 5,762,609 A | 6/1998 | Benaron et al. | |
| 5,762,613 A | 6/1998 | Sutton et al. | |
| 5,769,791 A | 6/1998 | Benaron et al. | |
| 5,772,597 A | 6/1998 | Goldberger et al. | |
| 5,800,350 A * | 9/1998 | Coppleson et al. | 600/372 |
| 5,807,261 A | 9/1998 | Benaron et al. | |
| 5,817,093 A | 10/1998 | Williamson et al. | |
| 5,843,000 A | 12/1998 | Nishioka et al. | |
| 5,961,458 A | 10/1999 | Carroll | |
| D424,693 S | 5/2000 | Pruter | |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,484,050 B1 | 11/2002 | Carroll et al. | |
| D487,039 S | 2/2004 | Webster et al. | |
| 6,689,128 B2 * | 2/2004 | Sliwa et al. | 606/41 |
| 6,697,666 B1 | 2/2004 | Richards-Kortum et al. | |
| 6,718,196 B1 | 4/2004 | Mah et al. | |
| D496,997 S | 10/2004 | Dycus et al. | |
| D499,181 S | 11/2004 | Dycus et al. | |
| 6,837,887 B2 * | 1/2005 | Woloszko et al. | 606/41 |
| 6,881,213 B2 | 4/2005 | Ryan et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,232,440 B2 * | 6/2007 | Dumbauld et al. | 606/51 |
| D564,662 S | 3/2008 | Moses et al. | |
| D576,932 S | 9/2008 | Strehler | |
| 7,449,008 B2 | 11/2008 | Hochman | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| 2003/0004407 A1 | 1/2003 | Carroll et al. | |
| 2003/0045798 A1 | 3/2003 | Hular et al. | |
| 2005/0261568 A1 | 11/2005 | Hular et al. | |
| 2007/0282320 A1* | 12/2007 | Buysse et al. | 606/34 |
| 2008/0306391 A1 | 12/2008 | Hular et al. | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2008142467 | 6/2008 |
| JP | 2001231870 | 8/2011 |
| SU | 166452 | 11/1964 |
| SU | 401367 | 11/1974 |
| SU | 727201 | 4/1980 |
| WO | WO00/36985 | 6/2000 |
| WO | WO2010/035831 | 4/2010 |

OTHER PUBLICATIONS

U.S. Appl. No. 08/483,742, filed Jun. 7, 1995, Roger A. Stern.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.

(56) References Cited

OTHER PUBLICATIONS

U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/343,788, filed Jan. 5, 2012, William O. Reid, Jr.
U.S. Appl. No. 13/343,798, filed Jan. 5, 2012, William O. Reid, Jr.
U.S. Appl. No. 13/344,753, filed Jan. 6, 2012, Lee et al.
U.S. Appl. No. 13/344,790, filed Jan. 6, 2012, Lee et al.
U.S. Appl. No. 13/400,223, filed Feb. 20, 2012, Anthony B. Ross.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,307, filed May 22, 2012, Casey M. Ladtkow.
U.S. Appl. No. 13/477,320, filed May 22, 2012, Joseph D. Brannan.
U.S. Appl. No. 13/483,858, filed May 30, 2012, Francesca Rossetto.
U.S. Appl. No. 13/488,964, filed Jun. 5, 2012, Steven P. Buysse.
U.S. Appl. No. 13/525,853, filed Jun. 18, 2012, Joseph A. Paulus.
U.S. Appl. No. 13/526,676, filed Jun. 19, 2012, Francesca Rossetto.
U.S. Appl. No. 13/539,650, filed Jul. 2, 2012, Joseph A. Paulus.
U.S. Appl. No. 13/539,690, filed. Jul. 2, 2012, Steven P. Buysee.
U.S. Appl. No. 13/539,725, filed Jul. 2, 2012, Steven P. Buysee.
U.S. Appl. No. 13/539,875, filed Jul. 2, 2012, Mani N. Prakash.
U.S. Appl. No. 13/551,005, filed Jul. 17, 2012, Chris Rusin.
U.S. Appl. No. 13/567,624, filed Aug. 6, 2012, Mani N. Prakash.
U.S. Appl. No. 13/568,679, filed Aug. 7, 2012, Robert J. Behnke, II.
U.S. Appl. No. 13/596,785, filed Aug. 28, 2012, Richard A. Willyard.
U.S. Appl. No. 13/598,141, filed Aug. 29, 2012, Kenlyn S. Bonn.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite-Element Codes to Model Electrical Heating and Non•L1near Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

(56) References Cited

OTHER PUBLICATIONS

Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medttex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shanga CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
P.R. Stauffer et al.; "Phantom and Animal Tissues for Modelling the Electrical Properties of Human Liver", International Journal of Hyperthermia, 2003, vol. 19, No. 1, pp. 89-101; Taylor and Francis Healthsciences; United Kingdom.
Palazzo et al., "Randomized clinical trial of LigaSure™ versus open haemorrhoidectomy" British Journal of Surgery 2002,89,154-157 Innovations in Electrosurgery Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis™ Technology (Date Unknown). "Overcoming the Challenge" located at: <http://www.urologix.com!medicaUtechnology.html> Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.

(56) References Cited

OTHER PUBLICATIONS

Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated,Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.

(56) References Cited

OTHER PUBLICATIONS

European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Oct. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009392.1 extended dated Sep. 19, 2011.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11000669.9 extended dated Jun. 30, 2011.
European Search Report EP 11001596.3 extended dated Jul. 4, 2011.
European Search Report EP 11001872.8 extended dated Jul. 6, 2011.
European Search Report EP 11004942 dated Oct. 4, 2011.
European Search Report EP 11009036.2 dated Feb. 13, 2012.
European Search Report EP 11010024.5 dated Apr. 20, 2012.
European Search Report EP 11010046.8 dated Apr. 17, 2012.
European Search Report EP 11010093.0 dated Mar. 27, 2012.
European Search Report EP 11010175.5 dated May 10, 2012.
European Search Report EP 11010176.3 dated Apr. 2, 2012.
European Search Report EP 11010177.1 dated May 10, 2012.
European Search Report EP 11174318.3 dated Nov. 7, 2011.
European Search Report EP 11185926.0 dated Feb. 3, 2012.
European Search Report EP 12000334.8 dated May 4, 2012.
European Search Report EP 12000335.5 dated May 10, 2012.
European Search Report EP 12000336.3 dated May 14, 2012.
European Search Report EP 12001841.1 dated Jul. 16, 2012.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.

* cited by examiner

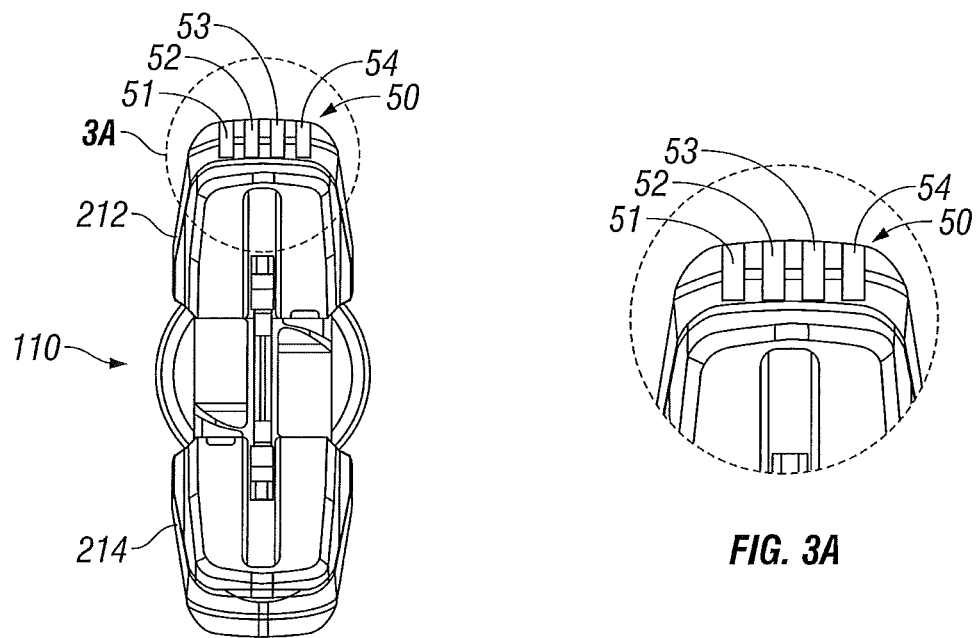
FIG. 3
FIG. 3A
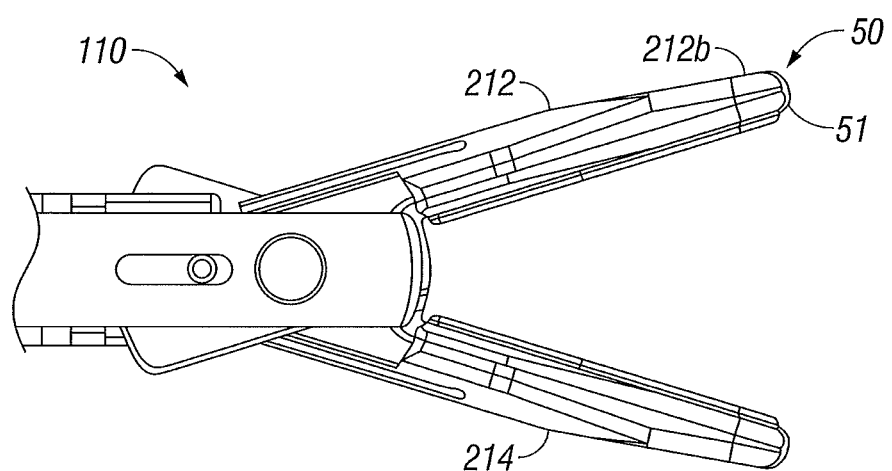
FIG. 4

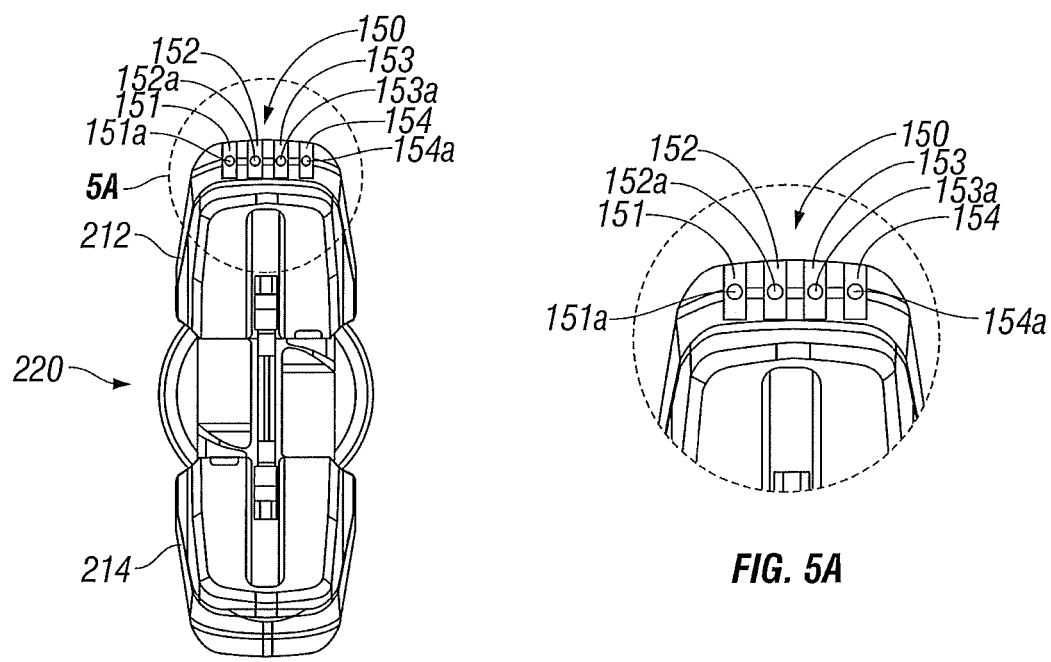
FIG. 5
FIG. 5A
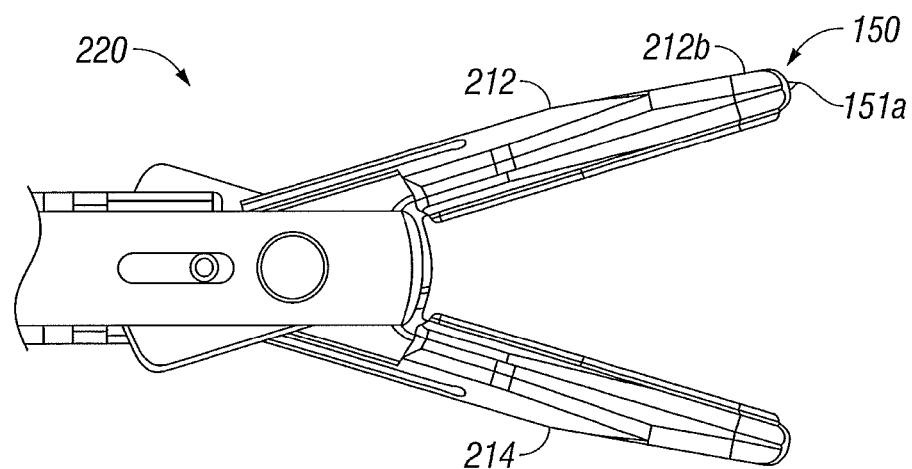
FIG. 6

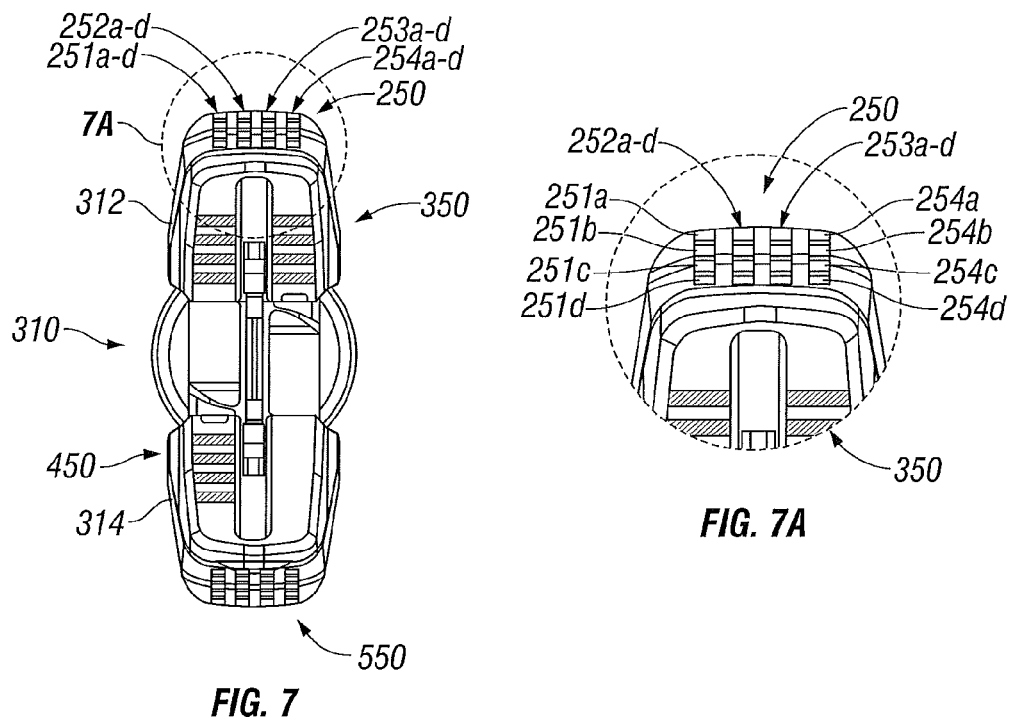
FIG. 7
FIG. 7A
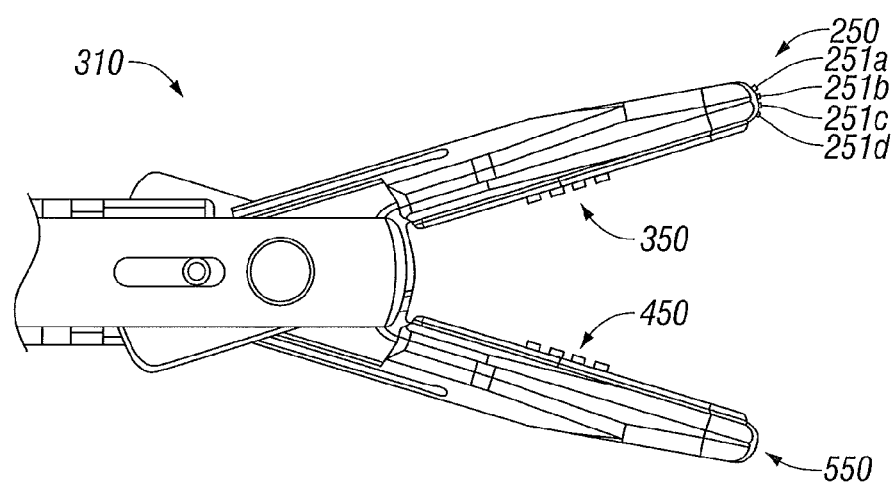
FIG. 8

ENDOSCOPIC INSTRUMENT FOR TISSUE IDENTIFICATION

CROSS-REFERENCE TO RELATED APPLICATIONS

This document is a divisional of U.S. patent application Ser. No. 12/366,298 filed Feb. 5, 2009 and entitled "Endoscopic Instrument for Tissue Identification," which claims the benefit of priority to U.S. Provisional Application Ser. No. 61/026,788 entitled "ENDOSCOPIC INSTRUMENT FOR TISSUE IDENTIFICATION" filed Feb. 7, 2008 by Mani N. Prakash et al, both of which are incorporated by reference herein.

BACKGROUND

1. Technical Field

The present disclosure relates to open or endoscopic instruments and method for treating tissue, and more particularly, the present disclosure relates to surgical instruments including an assembly for determining tissue type and the condition of the tissue being treated utilizing electrical property measurements of the tissue.

2. Background of Related Art

A hemostat or forceps is a simple plier-like tool that uses mechanical action between its jaws to constrict vessels and is commonly used in open surgical procedures to grasp, dissect and/or clamp tissue. Electrosurgical forceps utilize both mechanical clamping action and electrical energy to affect hemostasis by heating the tissue and blood vessels to coagulate, cauterize and/or seal tissue.

Over the last several decades, more and more surgeons are complementing traditional open methods of gaining access to vital organs and body cavities with endoscopes and endoscopic instruments that access organs through small puncture-like incisions. Endoscopic instruments are inserted into the patient through a cannula, or port, that has been made with a trocar. Typical sizes for cannulas range from three millimeters to twelve millimeters. Smaller cannulas are usually preferred, which, as can be appreciated, ultimately presents a design challenge to instrument manufacturers who must find ways to make surgical instruments that fit through the cannulas.

As mentioned above, by utilizing an electrosurgical instrument, a surgeon can either cauterize, coagulate/desiccate and/or simply reduce or slow bleeding, by controlling the intensity, frequency and duration of the electrosurgical energy applied through the jaw members to the tissue. The electrode of each jaw member is charged to a different electric potential such that when the jaw members grasp tissue, electrical energy can be selectively transferred through the tissue.

Bipolar electrosurgical instruments are known in the art, as are other electrosurgical instruments. Commonly owned U.S. Patent Application Publication No. 2007-0062017, discloses a bipolar electrosurgical instrument. Conventional bipolar electrosurgical instruments may include a cutting blade, fluid applicator, stapling mechanism or other like feature, in various combinations.

Different types of tissues, i.e. vessels, ligaments, may require different energy delivery configurations to effect proper sealing. While a specific energy delivery configuration may be adequate for treating an artery or vein, the same energy delivery configuration may not be suitable for treating a ligament. Although a majority of the time the type of tissue being treated is either known or visually apparent, there may be instances where a surgeon is unable to visually determine the type of tissue being sealed. Treating non-target type tissue with an energy configuration configured for a target type tissue may cause damage to the non-target tissue and/or result in failure to effect proper treatment.

Traditional methods for identifying tissue within the body are based on sensing physical characteristics or physiological attributes of body tissue, and then distinguishing normal from abnormal states from changes in the characteristic or attribute. For example X-ray techniques measure tissue physical density, ultrasound measures acoustic density, and thermal sensing techniques measures differences in tissue heat. A measurable electrical property of tissue is its impedance; i.e., the resistance tissue offers to the flow of electrical current through it. Values of electrical impedance of various body tissue are well known through studies on intact human tissue or from excised tissue made available following therapeutic surgical procedures.

Various methods and apparatus for measuring tissue electrical properties are known. For example, U.S. Pat. No. 5,380,429 to Withers, discloses a method and apparatus for displaying multi-frequency bio-impedance, and U.S. Patent Publication No. 2006/0004300, discloses a method of multi-frequency bio-impedance determination.

Once the type of tissue is identified, determining the condition or state of the tissue is important in effectively and properly treating the tissue. Diseased, ischemic, or otherwise compromised tissue may not adequately seal, or may require alteration to the energy delivered to the tissue. It is well documented that a decrease in electrical impedance occurs in tissue as it undergoes cancerous changes. Using any of the known methods for measuring tissue impedance, the tissue impedance may be measured, and the resulting measurements may be compared against known impedance measurements for like tissue. Difference between the readings may be used to indicate the condition of the tissue. Thus, knowledge of the electrical properties of tissue may be used to identify the type of tissue and/or the condition of that tissue.

SUMMARY

The present disclosure relates to surgical instruments including an assembly for determining tissue type and the condition of the tissue being treated utilizing tissue electrical property measurements.

Provided is a bipolar forceps including a handle, a shaft extending from the handle and having opposing jaw members at a distal end thereof, wherein the jaw members are configured for sealing tissue, and an electrode assembly for measuring an electrical property of a target tissue, the electrode assembly being mounted on at least one of said opposing jaw members.

The electrode assembly includes a plurality of electrodes and is configured to be operably connected to a processing unit. The processing unit may be configured to selectively measure at least one of an impedance, conductance and capacitance of the target tissue. The processing unit may be configured to determine a type of target tissue and/or a condition of the target tissue. The processing unit may be configured to alert a user when a predetermined condition has been satisfied. The forceps may be operably connectable to a generator. The generator may include a processing unit for determining tissue impedance.

Also provided is a method for identifying and treating tissue including providing a electrosurgical treatment device including an electrode assembly for measuring one or more electrical properties of a target tissue, the electrode assembly being mounted on a distal end thereof, measuring the one or more electrical characteristics of the target tissue, comparing the measured electrical property values of the target tissue against electrical property values of known tissue types, identifying a tissue type of the target tissue, adjusting an energy delivery configuration of the electrosurgical treatment device to the type of target tissue, and activating the electrosurgical treatment device to treat the target tissue.

The electrode assembly may include one or more electrodes. The electrode assembly includes a base having an electrode extending coaxially therethrough. The coaxially extending electrode may be operably connected to a high frequency generator. The high frequency generator may be capable of generating a frequency between 30 MHz and 30 GHz. The method may further include measuring an electrical property of the target tissue following treatment, and the determining the effectiveness of the treatment.

Further provided is a system for identifying and treating tissue including an electrosurgical treatment device, a generator operably connected to the electrosurgical treatment device for delivering electrosurgical energy thereto, an electrode assembly extending from a distal end of the electrosurgical treatment device, and a processing unit operably connected to the electrode assembly for measuring tissue one or more electrical properties of the tissue. The electrode assembly may be selectively extendable from the distal end of the electrosurgical treatment device and may include an electrode extending coaxially therethrough. The electrode may be operably connected to a high frequency generator. The electrode assembly may instead include at least a pair of electrodes or an array of electrodes.

A system for identifying tissue is also provided including a housing, an elongated body extending distally therefrom, the elongated body defining at least one lumen therethrough, and a probe operably extendable through the at least one lumen, the probe including at least one electrode determining at least one electrical property of tissue. The at least one electrode may extend coaxially through the probe. The system may further include a processor configured for identifying tissue using the determined electrical property. The array of electrodes may include at least four electrodes arranged linearly. The array of electrodes may instead include a plurality of electrodes arranged in an array.

BRIEF DESCRIPTION OF THE DRAWINGS

Various embodiments of the subject instrument are described herein with reference to the drawings wherein:

FIG. 3 is an enlarged front view of a jaw member including the multi-electrode assembly;

FIG. 3A is an enlarged view of the indicated area of detail of FIG. 3;

FIG. 4 is a side elevational view of the jaw member of FIG. 3;

FIG. 5 is an enlarged front elevational view of an alternate embodiment of a jaw member including another multi-electrode assembly for measuring tissue impedance;

FIG. 5A is an enlarged view of the indicated area of detail of FIG. 5;

FIG. 6 is a side elevational view of the jaw member of FIG. 5;

FIG. 7 is an enlarged front elevational view of yet another jaw member according to the present disclosure including yet another multi-electrode electrode assembly;

FIG. 7A is an enlarged view of the indicated area of detail of FIG. 7;

FIG. 8 is a side elevational view of the jaw member of FIG. 7;

DETAILED DESCRIPTION

Figure 1A:
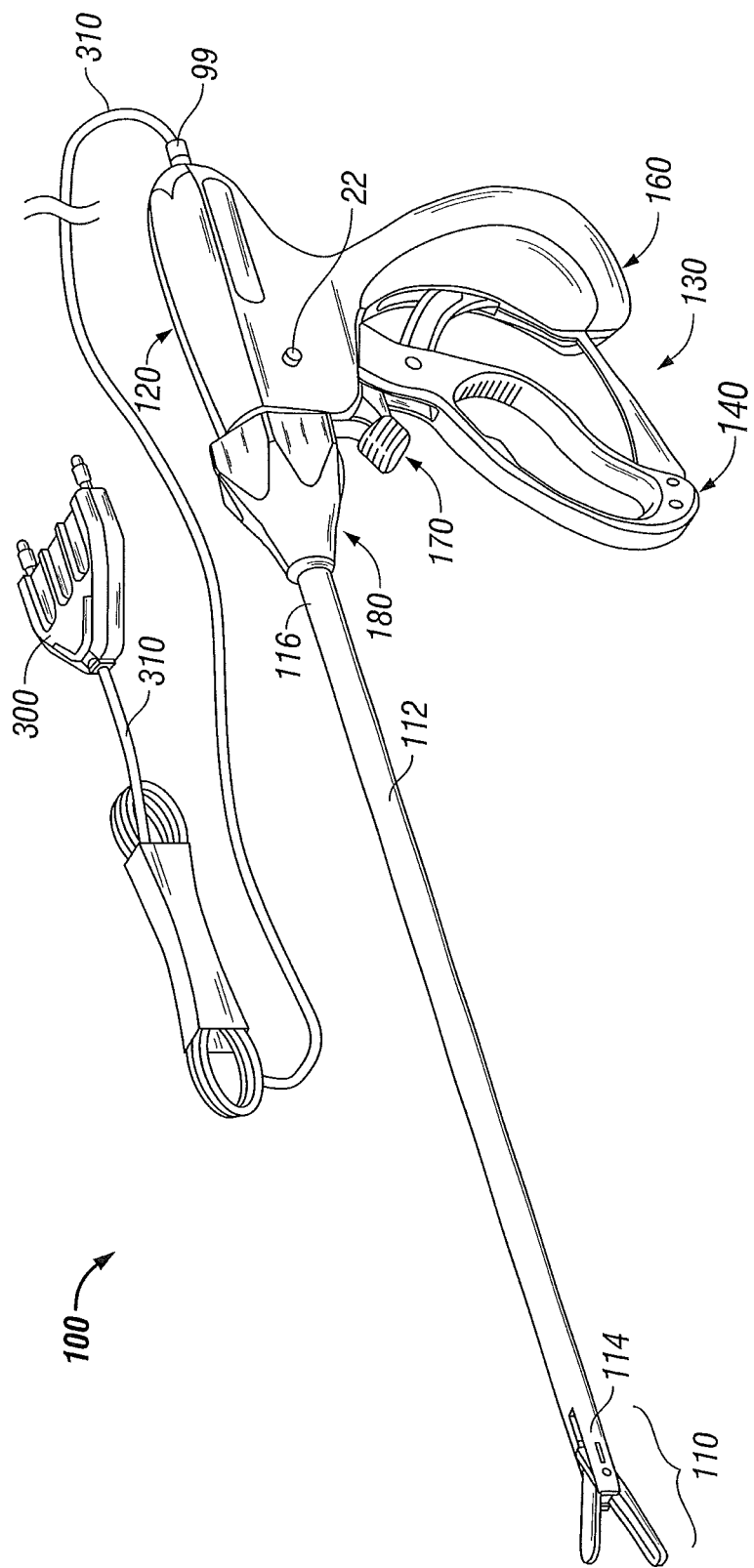
FIG. 1A is a left, perspective view of an endoscopic bipolar forceps including a multi-electrode assembly for measuring tissue impedance according to an embodiment of the present disclosure.
Figure 1B:
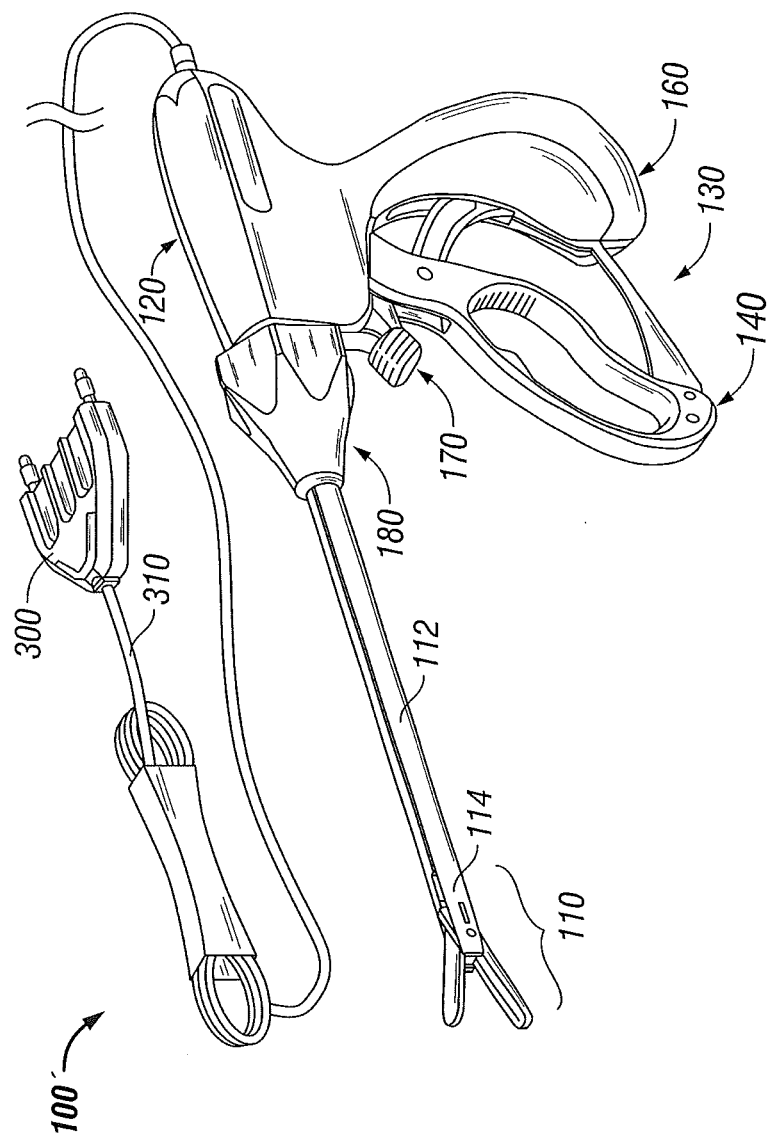
FIG. 1B is a left, perspective of an open bipolar forceps including a multi-electrode assembly for measuring tissue impedance according to an embodiment of the present disclosure.

Referring now to FIGS. 1-4, an embodiment of an electrosurgical instrument according to the present disclosure is shown generally as bipolar forceps 100. Bipolar forceps 100 include a housing 120, a handle assembly 130, a rotating assembly 180, a trigger assembly 170 and an end effector assembly 110 that mutually cooperate to grasp, seal and divide tubular vessels and vascular tissue. Although the following disclosure focuses predominately on discussion of a bipolar forceps 100 for use in connection with endoscopic surgical procedures, an open forceps 100' are also contemplated for use in connection with traditional open surgical procedures and are shown by way of example in FIG. 1B. For the purposes herein, the endoscopic version is discussed in detail; however, it is contemplated that open forceps 100' also include the same or similar operating components and features as described below.

Bipolar forceps 100, 100' are substantially identical in form and function to bipolar forceps 10, 10' described in detail in commonly owned, U.S. Patent Publication No. 2007-0062017. Thus, the form and function of bipolar forceps 100, 100' will be discussed only to the extent necessary to describe the improvement thereto. The aspects of the present disclosure may be incorporated into any suitable electrosurgical instrument.

Figure 2:
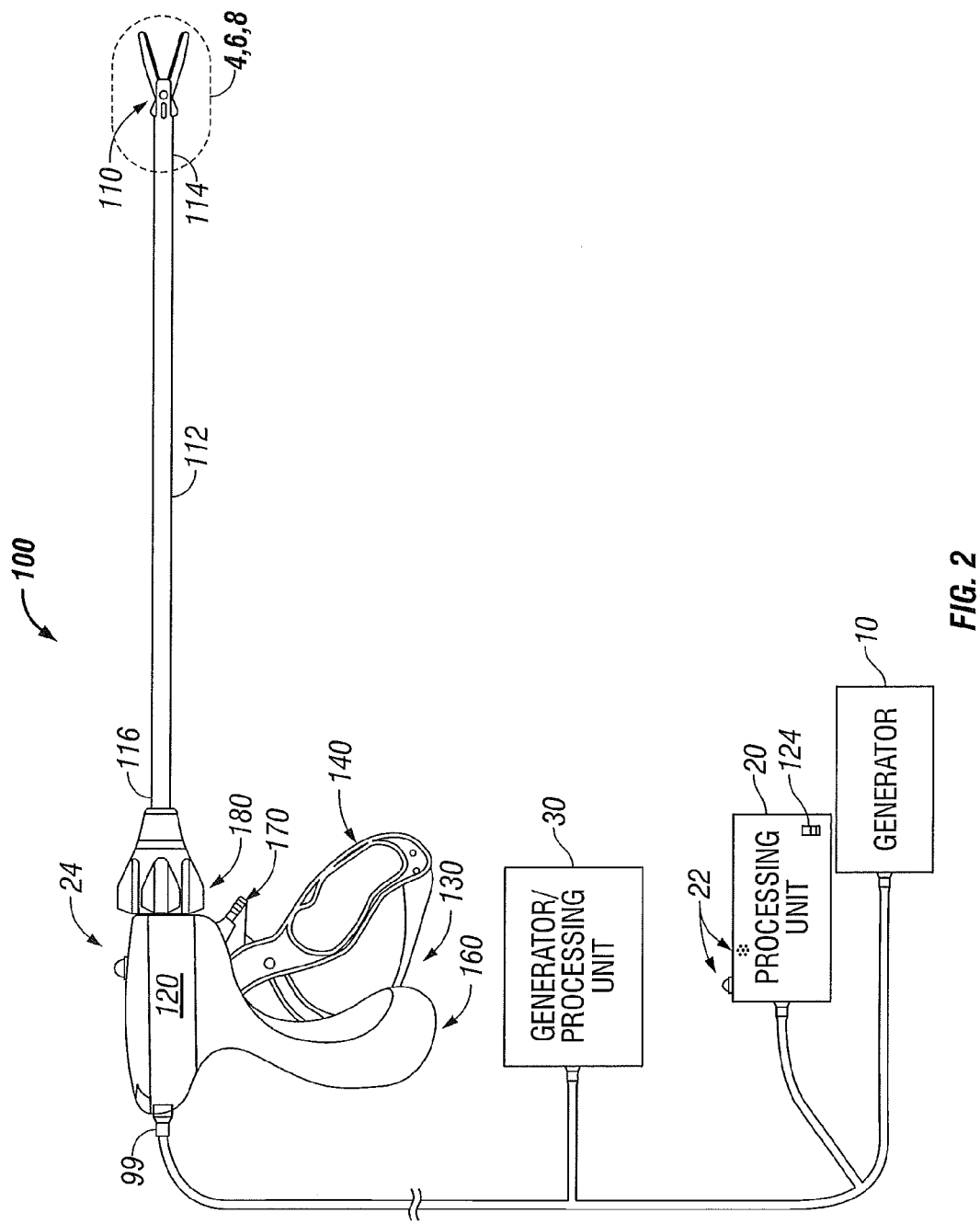
FIG. 2 is a schematic illustration of an electrosurgical system including the endoscopic bipolar forceps of FIG. 2A.

Turning now to FIGS. 1A and 2, forceps 100 includes a shaft 112 that has a distal end 114 dimensioned to mechanically engage the end effector assembly 110 and a proximal end 116 that mechanically engages housing 120. In the drawings and in the descriptions that follow, the term "proximal", as is traditional, will refer to the end of the forceps 100 that is closer to the user, while the term "distal" will refer to the end which is further from the user.

As seen in FIG. 1A, handle assembly 130 includes a fixed handle 160 and a movable handle 140. Fixed handle 160 is integrally associated with housing 120 and handle 140 is movable relative to fixed handle 160. Rotating assembly 80 is preferably attached to a distal end of housing 120 and is rotatable approximately 180 degrees in either direction about a longitudinal axis "A".

Turning briefly to FIGS. 3-4, end effector assembly 110 includes first and second jaw members 212, 214. First and second jaw members 212, 214 are operably connected to handle 140 (FIG. 1A). First and second jaw members 212, 214 are configured to approximate towards one another upon activation of handle 140. First and second jaw members 212, 214 cooperate to grasp and seal target tissue therebetween.

As best seen in FIGS. 1A and 2, forceps 100 also include an electrical interface or plug 300 that connects the forceps 100 to a source of electrosurgical energy, e.g., a generator 10, and a processing unit 20. Generator 10 and processing unit 20 may be combined to form a single generator/processing unit 30. For ease of disclosure, further references to processing unit 20 may also be applicable to generator/processing unit 30. Generator 10 may be one of many sold by Valleylab—a division of Tyco Healthcare LP, located in Boulder Colo., used as a source of electrosurgical energy, e.g., FORCE EZ™ Electrosurgical Generator, FORCE FX™ Electrosurgical Generator, FORCE 1C™, FORCE 2™ Generator, SurgiStat™ II. One such system is described in commonly-owned U.S. Pat. No. 6,033,399 entitled "ELECTROSURGICAL GENERATOR WITH ADAPTIVE POWER CONTROL". Other systems have been described in commonly-owned U.S. Pat. No. 6,187,003 entitled "BIPOLAR ELECTROSURGICAL INSTRUMENT FOR SEALING VESSELS".

Generator 10 and/or generator/processing unit 30 may include various safety and performance features including isolated output, independent activation of accessories, and the Valleylab REM™ Contact Quality Monitoring System, which may substantially reduce the risk of burns under the patient return electrode. The electrosurgical generator may include Valleylab's Instant Response™ technology features that provides an advanced feedback system that senses changes in tissue 200 times per second and adjusts voltage and current to maintain appropriate power.

Processing unit 20 is operably connected to an electrode assembly 50 (FIG. 3). As will be discussed in further detail below, electrode assembly 50 may be mounted on a distal end of forceps 100. Processing unit 20 operates in a manner similar to known tissue impedance measuring devices. Briefly, a predetermined energy signal is produced by processing unit 20 and applied to the target tissue (not explicitly shown) through electrode assembly 50. The resultant electrical response of the tissue to the signal may then be measured and converted into an impedance value. By comparing the tissue impedance measurements with known tissue impedance measurements processing unit 20 may determine the type of tissue being in contact with electrode assembly 50.

The electrical current produced by processing unit 20 may vary depending on the type of tissue being identified. Processing unit 20 may configured to produce AC and/or DC current. Processing unit 20 may be configured to generate an electrical signal having a frequency ranging from RF (100 kHz) upwards of microwaves (low MHz to GHz). Depending on the application processing unit 20 may produce a signal of constant frequency, or may instead perform a frequency sweep. Bipolar forceps 100 may include more than one electrode assembly 50 connected to processing unit 20 for measuring tissue impedance. As will be discussed in further detail below, the one or more electrode assemblies 50 may include different electrode configurations depending on the tissue type and/or signal frequency being tested. Processing unit 20 may include any suitable methods of increasing the accuracy and consistency of the tissue electrical property measurements, e.g. filters and multi-frequency readings.

Processing unit 20 may operate in a number of modes. Processing unit 20 may be configured to alert a user when electrode assembly 50 has contacted a specific tissue type. In this manner, a user would set processing unit 20 to scan for a particular tissue type. Processing unit 20 would produce an electrical signal configured for best identifying the tissue type. The electrical signal produced by processing unit 20 may be manually determined by the user or may instead be automatically determined by processing unit 20. The electrical signal produced may include a specific frequency or range of frequencies and/or may include a specific signal configuration. Electrode assembly 50 may be placed in contact over a portion of tissue. As electrode assembly 50 contacts tissue of the target type, as determined by processing unit 20 by comparing the electrical property measurements with known electrical property measurements of like tissue, processing unit 20 may alert the user. The alert may be audio and/or visual. An audio and/or visual indicator 22, 24 (FIG. 2) may be included in/on processing unit 20 and/or bipolar forceps 100.

Identifying tissue type by comparing the electrical property measurements of the tissue with electrical property measurements from known tissue type requires the availability of electrical property measurements of known tissue. These measurements may not always be available, or may vary depending on the environment in which the target tissue is situated. For example, tissue located within the digestive tract and exposed to digestive enzymes may have different electrical property measurements from tissue exposed to air. When implementing the comparative technique described above, knowledge of the electrical property of the tissue exposed to digestive enzymes would be of little use when compared to the electrical properties of tissue exposed to air. When electrical property measurements of known tissue are not available, the type of tissue may be determined by comparing the electrical property measurements of the target tissue with the electrical property measurements of the surrounding tissue. Since fat exhibits different electrical properties from muscle, and muscles exhibits different electrical properties that connective tissue, by comparing the relative electrical property measurements of different tissue types within the same environment, i.e. saturated in digestive enzymes, or exposed to air, the differences in the relative electrical property measurements of the various tissues may be used to distinguish the various tissue types. Another example is the difference between a suspicious mass and the surrounding normal tissue may be used to determine its nature as benign or malignant.

Alternatively, processing unit 20 may be configured to determine the type of tissue in contact with electrode assembly 50. In this manner, processing unit 20 produces an electrical signal spanning a wide range of frequencies and/or wave configurations. The range of frequencies and/or wave configurations may be limited by the user. As before, the tissue electrical property measurements (magnitude and/or phase) are compared against electrical property measurements for known tissue. Once processing unit 20 has determined the type of tissue the user may be alerted. The alert may be audio and/or visual.

Once the type of tissue is known, whether through visual inspection or tissue impedance measurements, the condition of the tissue may also be determined. Using techniques similar to that described above, the condition of the tissue may also be determined. Knowing the type of tissue being examined is not necessary; however, it permits a user to limit the frequency range and/or signal configuration of the electrical signal applied to the tissue, thereby reducing the time for a result. The condition of the tissue may be determined by comparing the electrical property measurements with electrical property measurements of tissue of a known condition. In addition, the condition of the tissue may be determined by comparing the electrical property measurements of portions of the same tissue. Processing unit 20 may provide the user with an audio and/or visual alert as to the condition of tissue in contact with electrode assembly 50.

Tissue has many electrical properties and there are many known methods for measuring these electrical properties. Although the following discussion will relate to a four-electrode method of measuring tissue impedance, other methods of measuring tissue electrical properties have been contemplated by the present disclosure. In the four-electrode method, four equidistant electrodes are placed in contact with or penetrate into the tissue to be tested. In one procedure utilizing the four-electrode method, a sinusoidal voltage is applied to the tissue across two electrodes and the resultant sinusoidal current flow through the tissue is measured. The magnitude of the tissue impedance may be determined as the ratio of the root-mean-square (RMS) voltage and the current values. The phase angle of the tissue impedance may be determined as the delay in radians of the peak sinusoidal current with respect to the peak sinusoidal voltage. By comparing the resulting impedance values with known values for various body tissue, the tissue type may be determined. It should be appreciated that the aspects of the present disclosure should not be limited to the methods of determining tissue impedance disclosed herein. Any suitable method for measuring tissue electrical properties may be incorporated into the embodiments of the present disclosure.

Turning now to FIGS. 3-8, various embodiments of opposing jaw members including one or more multi-electrode assemblies that operate in a manner as discussed above are shown. Referring initially to FIGS. 3-4, end effector 110 of bipolar forceps 100 includes an electrode assembly 50. Electrode assembly 50 is mounted on a distal end 212*b* of first jaw member 212. As will be discussed below, alternate embodiments of bipolar forceps 100 may include a plurality of electrode assemblies mounted at various locations on first and/or second jaw members 212, 214. Electrode assembly 50 includes four electrodes 51, 52, 53, 54. In the illustrated embodiment, electrodes 51, 52, 53, 54 form substantially planar members having a substantially similar size and configuration. Electrodes 51, 52, 53, 54 are spaced an equidistance apart and may be formed of a metal, an alloy or other suitable material. Electrodes 51, 52, 53, 54 of electrode assembly 50 are operably connected to processing unit 20 (FIG. 3).

In operation, electrodes 51, 52, 53, 54 of electrode assembly 50 are placed in contact with the tissue to be identified. First and second jaw members 212, 214 may be in an open or closed condition. Processing unit 20 produces an electric signal that is directed into the target tissue through outer electrodes 51, 54. Processing unit 20 may be configured to continuously produce a signal, or instead bipolar forceps 100 may include a button or lever 122, 124 mounted on housing 120 (FIG. 1A) and/or processing unit 20 (FIG. 2) for activating processing unit 20. As discussed above, depending on the application, the electric signal may be of a specific frequency or range of frequencies and of any configuration. The respective portion of tissue disposed between outer electrode 51 and inner electrode 52, and outer electrode 54 and inner electrode 53 functions to complete a circuit path therebetween. These portions of tissue produce characteristic tissue responses based on the signals delivered to electrodes 51, 52, 53, 54 by processing unit 20. The resulting tissue response is acquired by inner electrodes 52, 53. Also, as discussed above, the measurements of the tissue response may be used to calculate the tissue impedance. By comparing the tissue impedance values of the target tissue with impedance values of known tissue, the type of tissue being contacted (e.g., lung, liver, muscle, etc.) may be determined.

As discussed above, once the tissue type has been determined, either through visual inspection, by comparing tissue electrical property measurements or with another suitable method, the condition of the tissue may also be determined. By directing an electric signal of a frequency or range of frequencies configured for the particular tissue type being tested and measuring the resultant impedance values, the condition of the tissue may be determined. For example, healthy tissue may be distinguished from cancerous tissue. Additionally, the stage of development of the cancer may also be determinable using the tissue impedance measurements.

Once the tissue type and condition of the tissue have been identified, bipolar forceps 100 may operate as a conventional bipolar vessel sealer. The energy delivery configuration of generator 10 may be adjusted in accordance with the identified tissue type being sealed. The closure pressure of first and second jaw members 212, 214 may also be adjusted in view of the type of tissue being sealed and/or the condition of the tissue being sealed.

While four electrodes, 51, 52, 53, 54 are shown as forming a part of multi-electrode assembly 50, any suitable number of electrodes may be used either greater than or less than four in forming multi-electrode assembly 50.

Turning now to FIGS. 5-6, in an alternate embodiment of an end effector of the present disclosure, end effector 220 includes electrode assembly 150 mounted on a distal end 212*b* of first jaw member 212. Alternately, electrode assembly 150 may be mounted on distal end 214*b* of second jaw member 214. Electrode assembly 150 includes electrodes 151, 152, 153, 154. Electrodes 151, 152, 153, 154 include piercing or penetrating members 151*a*, 152*a*, 153*a*, 154*a*, respectively, for penetrating the target tissue to be identified. By using piercing members 151, 152, 153, 154 to penetrate the tissue a relatively truer or more accurate tissue impedance measurement may be obtained. Piercing members 151*a*, 152*a*, 153*a*, and 154*a* may be of any suitable dimension and of any suitable configuration. In an alternate embodiment, electrodes 151, 152, 153, 154 and/or piercing members 151*a*, 152*a*, 153*a*, 154*a* may be selectively retractable and/or extendable.

With reference now to FIGS. 7-8, in another embodiment of an end effector of the present disclosure, end effector 310 includes electrode assembles 250, 350, 450, and 550. Electrode assemblies 250, 550 are each substantially similar to electrode assemblies 50, 150 described hereinabove, and will therefore only be described as relates to the differences therebetween. Electrode assembly 250 or 550 includes an array of electrodes 251*a-d*, 252*a-d*, 253*a-d*, 254*a-d* arranged in any suitable configuration (e.g. rectilinear) and in any suitable quantity. Electrodes 251*a-d*, 252*a-d*, 253*a-d*, 254*a-d* of electrode assembly 250 are each operably connected to processing unit 20 (FIG. 2). Processing unit 20 may be configured to selectively apply electric signals through any or all of electrodes 251*a-d*, 252*a-d*, 253*a-d*, 254*a-d* in a manner similar to that described above to determine impedance of a target tissue. The rectilinear array of electrode assembly 240 enables a user to select the electrode configuration best suited for measuring and identifying tissue of a particular type.

With continued reference to FIGS. 7-8, electrode assemblies 350, 450 are positioned on an inner surface of first and second jaw member 312, 314, respectively, e.g., on a tissue contacting surface thereof. Electrode assemblies 350, 450 operate in a manner substantially similar to electrode assemblies 250, 550 described hereinabove. By including electrode assemblies 350, 450 on an inner surface of first and second jaw member 312, 314, respectively, the type of tissue being grasped therebetween may be determined. Such identification of tissue may occur at any time prior to a sealing of the target tissue.

Electrode assemblies 50, 150, 250, 350, 450, 550 may also be used post-sealing to determine if a proper seal has been formed. By measuring the impedance of a post-sealing tissue, and comparing the impedance measurements thereof with known values of properly sealed tissue processing unit 20 (FIG. 2) may alert a user of the condition of the post-sealing tissue. Alternatively, processing unit 20 may compare the post-sealing impedance measurements of the tissue with the pre-sealing impedance measurements thereof to determine if a proper seal has been affected.

Referring now to FIGS. 9-12, another embodiment of the present disclosure is shown generally as endoscopic device 500. Briefly, endoscopic device 500 includes a housing 520 and an elongated tubular member 512 extending from the housing 520. Tubular member 512 defines a plurality of working channels or lumens 515a, 515b, 515c extending therethrough. Proximal end 516 of tubular member 512 mechanically engages or is supported on or by housing 520. Tubular member 512 may be rigid, flexible and/or selectively rigid. Housing 520 may include a steering mechanism 580 for controlling or articulating distal end 514 of tubular member 512 in any suitable manner. Working channels or lumens 515a, 515b, 515c may be configured to receive an endoscope, electrosurgical instrument, snare or the like therethrough.

Figure 9:
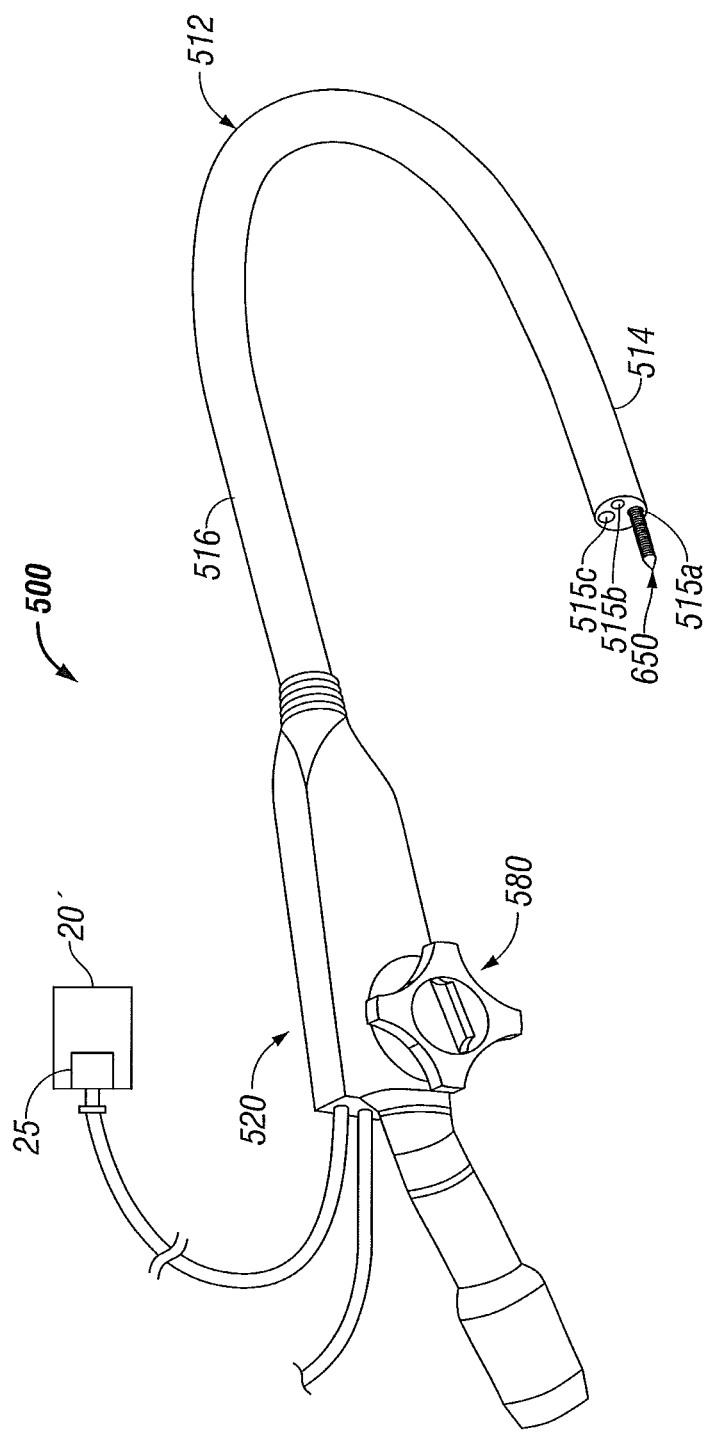
FIG. 9 is a perspective view of an alternate embodiment of an electrosurgical instrument extending through a working channel of an endoscope.
Figure 10:
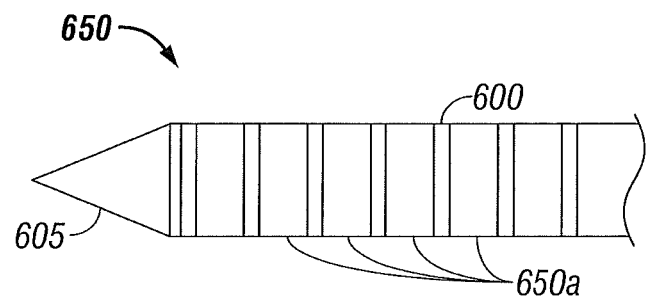
FIG. 10 is a enlarged side view of the electrode assembly of the endoscopic device of FIG. 9.

As seen in FIG. 9, an electrode assembly 650 extends through working channel or lumen 515a of tubular member 512. As seen in FIG. 10, electrode assembly 650 includes a plurality of electrodes 650a mounted about a probe-like base or core member 600. Electrodes 650a may be axially spaced apart from one another along a length of core member 600. Electrode assembly 650 may include a cauterization and/or sealing tip 605 for treating tissue. As seen in FIG. 10, tip 605 may be sharpened, tapered and/or beveled.

Electrode assembly 650 is operably connected to a processing unit 20' (see FIG. 9). Processing unit 20' is substantially similar to processing unit 20 described hereinabove and thus will not be described in further detail herein. Additionally, processing unit 20' may include a drive mechanism 25 for advancing and retracting multi-electrode assembly 650 from within channel 515a of tubular member 512.

Figure 11:
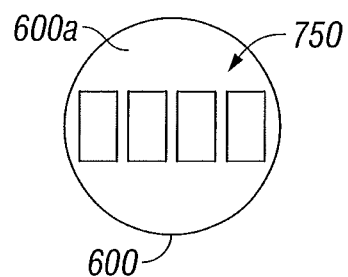
FIG. 11 is an enlarged end view of an alternate embodiment of an electrode assembly.
Figure 12:
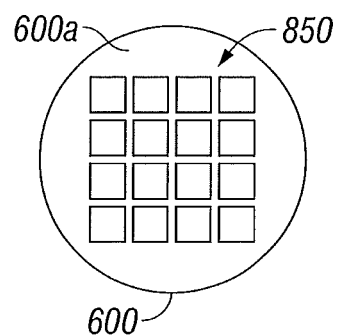
FIG. 12 is an enlarged end view of another embodiment of an electrode assembly.

Alternatively, as seen in FIGS. 11 and 12, base or core member 600 may include a flattened distal end surface 600a. Flattened distal end surface 600a may include multi-electrode assemblies of multiple configurations. As shown in FIG. 11, base member 600 may include a linear array of electrodes 750 provided on distal end surface 600a (e.g., an exemplary four electrodes being shown), or a grid-like or rectangular array of electrodes 850 provided on distal end surface 600a (e.g., an exemplary 4×4 rectangular array being shown) multi-electrode assembly 850. Electrode arrays 750, 850 operate in a manner similar to the multi-electrode assemblies or arrays described above and thus will not be described in further detail herein.

Figure 13A:
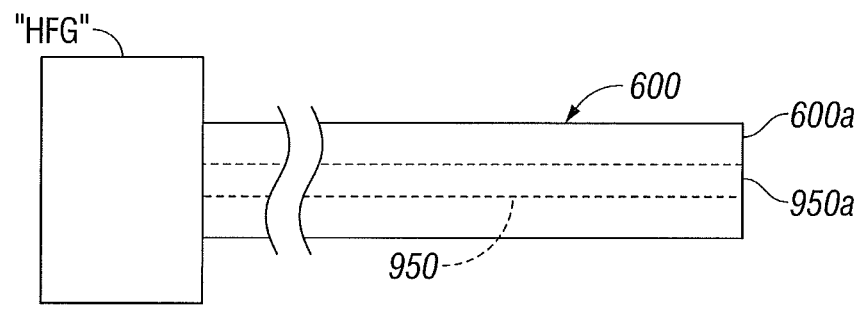
FIG. 13A is a side view of another embodiment of an electrode assembly.
Figure 13B:
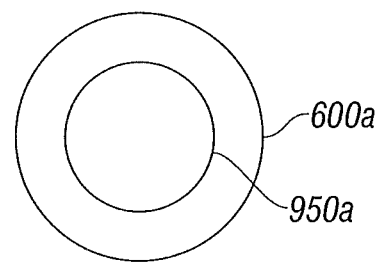
FIG. 13B is an enlarged distal end view of the electrode assembly of FIG. 13A.

With reference to FIGS. 13A and 13B, in yet another embodiment, base member 600 defines a sheath 602 that includes a coaxially electrode 950 extending a length thereof. In this manner, only a distal end 950a of electrode 950 is exposed. It is envisioned that distal end 950a of electrode 950 may form a pointed surface for penetrating tissue. Coaxially electrode 950 may be operably connected to a high frequency generator "HFG" capable of generating a signal between 30 MHz-30 GHz.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto. For example,

What is claimed is:

1. A bipolar forceps, comprising:
    a handle;
    a shaft extending from the handle and having opposing jaw members at a distal end thereof, wherein the jaw members are configured for sealing tissue; and
    an electrode assembly for measuring an electrical property of a target tissue, the electrode assembly including a plurality of electrodes mounted on a distal end of one of the opposing jaw members, the electrode assembly configured to apply electric signals to a target tissue through at least one of the plurality of electrodes and to receive the electric signals from the target tissue through at least another of the plurality of electrodes.

2. A bipolar forceps according to claim 1 wherein the electrode assembly is operably connected to a processing unit that is configured to selectively measure at least one of an impedance, conductance, and capacitance of the target tissue.

3. A bipolar forceps according to claim 2 wherein the processing unit is configured to determine a type or a condition of the target tissue.

4. A bipolar forceps according to claim 2 wherein the processing unit is configured to alert a user when a predetermined condition has been satisfied.

5. A bipolar forceps according to claim 1 wherein the forceps are operably connectable to a generator.

6. A bipolar forceps according to claim 5 wherein the generator includes a processing unit operable to determine tissue impedance.

7. A bipolar forceps according to claim 1, wherein the electrode assembly includes four electrodes.

8. A bipolar forceps according to claim 7, wherein the four electrodes are spaced an equidistance apart.

9. A bipolar forceps according to claim 1, wherein the plurality of electrodes are configured in a rectilinear array.

10. A bipolar forceps according to claim 1, wherein each of the electrodes includes a piercing member configured to penetrate target tissue.

11. A bipolar forceps according to claim 1, wherein the electrode assembly further includes a processing unit that is configured to selectively apply the electric signals through at least one of the electrodes.

12. A system for identifying and treating tissue, comprising:
    an electrosurgical treatment device;
    a generator operably connected to the electrosurgical treatment device for delivering electrosurgical energy thereto;
    an electrode assembly extending from a distal end of the electrosurgical treatment device, the electrode assembly including a core member and a plurality of electrodes mounted about the core member, the core member including an elongated electrode disposed coaxially therethrough and operable to treat tissue, the plurality of electrodes axially spaced apart from one another along a length of the core member and axially spaced from a distal end of the electrode assembly; and a processing unit operably connected to the electrode assembly for measuring one or more electrical properties of the tissue.

13. A system according to claim 12, wherein the electrode assembly is selectively extendable from the distal end of the electrosurgical treatment device.

14. A system for identifying tissue, the system comprising:

a housing;

an elongated body extending distally from the housing, the elongated body defining at least one lumen therethrough; and a probe operably extendable through the at least one lumen, the probe including a core member and a plurality of electrodes mounted about the core member, the core member including an elongated electrode disposed coaxially therethrough and operable to treat tissue, the plurality of electrodes axially spaced apart from one another along a length of the core member and axially spaced from a distal end of the probe, the plurality of electrodes configured to determine at least one electrical property of tissue.

15. A system according to claim 14, further comprising a processor configured to identify a type or a condition of the target tissue using the determined electrical property.

* * * * *